United States Patent
Moehl et al.

(10) Patent No.: US 9,060,893 B2
(45) Date of Patent: Jun. 23, 2015

(54) DELIVERY SYSTEM FOR A MEDICAL DEVICE AND METHOD FOR OPERATING A DELIVERY SYSTEM FOR A MEDICAL DEVICE

(75) Inventors: Raimund Moehl, Forch (CH); Amir Fargahi, Bülach (CH)

(73) Assignee: BIOTRONIK VI Patent AG, Baar (CH)

( * ) Notice: Subject to any disclaimer, the term of this patent is extended or adjusted under 35 U.S.C. 154(b) by 1336 days.

(21) Appl. No.: 12/486,426

(22) Filed: Jun. 17, 2009

(65) Prior Publication Data
US 2009/0319018 A1   Dec. 24, 2009

(30) Foreign Application Priority Data
Jun. 17, 2008   (DE) .................... 10 2008 002 472

(51) Int. Cl.
  *A61F 2/06*   (2013.01)
  *A61F 2/95*   (2013.01)
  *A61F 2/966*   (2013.01)
(52) U.S. Cl.
  CPC .. *A61F 2/95* (2013.01); *A61F 2/966* (2013.01)
(58) Field of Classification Search
  CPC .... A61F 2/966; A61F 2/95; A61F 2250/0092
  USPC ................ 623/1.11, 1.12; 606/108
  See application file for complete search history.

(56) References Cited

U.S. PATENT DOCUMENTS

| | | | |
|---|---|---|---|
| 5,693,083 A | 12/1997 | Baker et al. | |
| 2003/0109886 A1* | 6/2003 | Keegan et al. | 606/108 |
| 2003/0125790 A1* | 7/2003 | Fastovsky et al. | 623/1.11 |
| 2003/0153942 A1* | 8/2003 | Wang et al. | 606/200 |
| 2004/0236410 A1 | 11/2004 | Herweck | |
| 2005/0090890 A1* | 4/2005 | Wu et al. | 623/1.11 |
| 2005/0113902 A1* | 5/2005 | Geiser et al. | 623/1.11 |
| 2007/0055338 A1* | 3/2007 | Dorn | 623/1.11 |
| 2007/0168014 A1 | 7/2007 | Jimenez et al. | |
| 2007/0282420 A1 | 12/2007 | Gunderson | |

FOREIGN PATENT DOCUMENTS

| | | |
|---|---|---|
| DE | 19938377 | 8/1999 |
| DE | 10 2005 008 682 | 2/2005 |
| WO | WO 2004/098692 | 11/2004 |
| WO | WO 2006/036472 | 4/2006 |

OTHER PUBLICATIONS

European Patent Office, European Search Report dated Oct. 1, 2009 for European Application No. 09160157.5-2320.
German Patent Office, Search Report for Priority German Application No. 10 2008 002 472.4, Issued Apr. 22, 2009.

* cited by examiner

*Primary Examiner* — Katherine Dowe
(74) *Attorney, Agent, or Firm* — Greer, Burns & Crain, Ltd.

(57) ABSTRACT

The invention relates to a delivery system for a medical device and a method for operating a delivery system for a medical device, in particular a stent having a proximal end and a distal end, an inner shaft enclosing an inner lumen and an outer shaft surrounding the inner shaft in at least some areas and enclosing an intermediate lumen. One or more openings are provided in the inner shaft establishing a fluid connection between the inner lumen and the intermediate lumen.

14 Claims, 1 Drawing Sheet

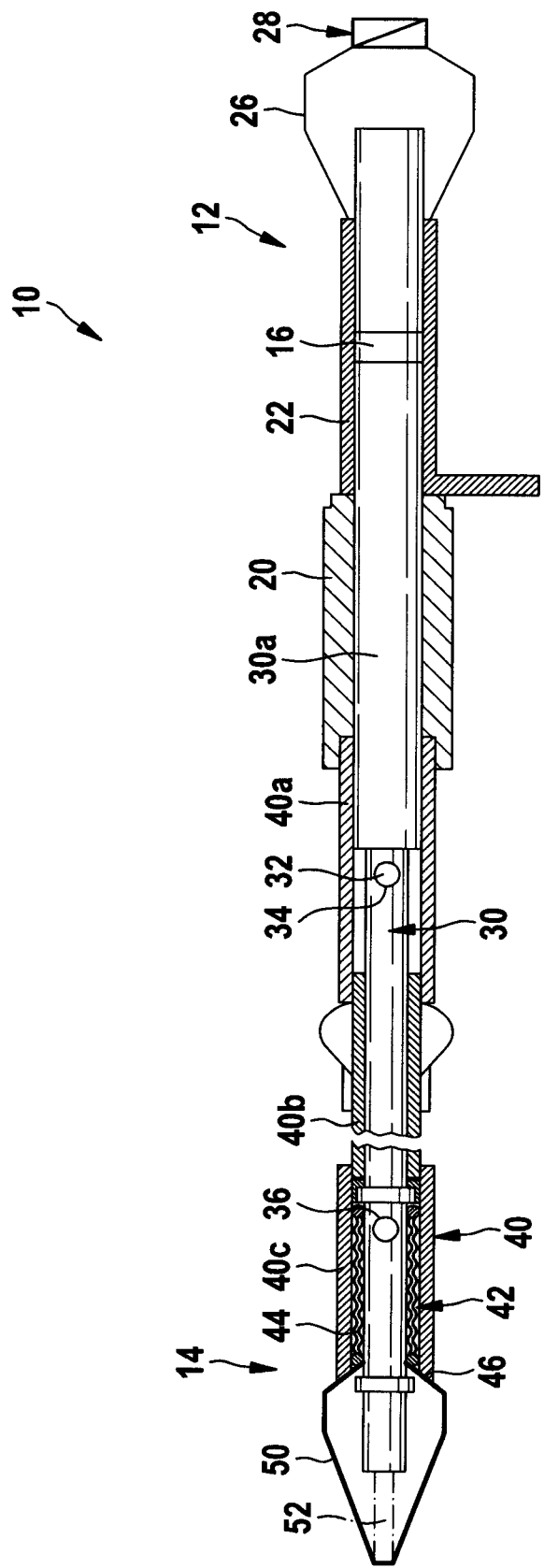

DELIVERY SYSTEM FOR A MEDICAL DEVICE AND METHOD FOR OPERATING A DELIVERY SYSTEM FOR A MEDICAL DEVICE

FIELD

The invention relates to a delivery system for a medical device and a method for operating a delivery system for a medical device according to the preambles of the independent claims.

BACKGROUND

There are known delivery systems for medical devices such as vascular supporting bodies (stents). To avoid introducing air into the vascular system, the lumens of a stent delivery system are rinsed with a saline solution and vented before being inserted. This permits rinsing and venting of the internal lumen in which the guide wire is guided or the intermediate lumen between the inner shaft and the outer shaft where the stent is arranged during delivery. The intermediate lumen cannot be vented with some of the known delivery systems. US 2007/0282420 A1 discloses a stent delivery system having vent and rinse openings in the outer shaft surrounding the stent on insertion.

There are other known delivery systems in which the guide wire lumen and the intermediate lumen can be vented by two separate connecting pieces in separate operations. Separate T-bodies through which a rinsing fluid can be supplied and the respective lumen can be vented are known.

The object of the present invention is to create a delivery system and a method for operating such a system with which simple handling and uncomplicated design of the delivery system are possible.

This object is achieved according to the invention by the features of the independent claims. Advantageous embodiments and advantages of the invention are derived from the additional claims and the description.

SUMMARY

A method for operating a delivery system for a medical device and a delivery system for a medical device, in particular a stent, are proposed, having a proximal end and a distal end, an inner shaft enclosing an inner lumen and an outer shaft surrounding the inner shaft in at least some areas, enclosing an intermediate lumen. One or more openings are provided in the inner shaft, establishing a fluid connection between the inner lumen and the intermediate lumen. Flushing or venting of the inner lumen and the intermediate lumen may therefore be performed with a single device. First, the inner lumen is accessible, and secondly, separate connections are not needed for rinsing and/or venting the inner lumen and the intermediate lumen. The design of the delivery device can therefore be simplified.

If a first opening can be arranged in proximity to a proximal end of the inner shaft and another opening can be arranged in proximity to a distal end, then the respective lumen can be rinsed and vented along its longitudinal extent. A coupling device for rinsing and/or venting the inner lumen and the intermediate lumen with a fluid may be provided on the proximal end. This arrangement allows a compact and convenient design of the delivery device. The coupling device may preferably be arranged on a connection piece of the inner lumen.

According to the proposed method for operating a delivery system for a medical device, rinsing and/or venting of the inner lumen and the intermediate lumen are performed in a single operation. Handling of the delivery system is thereby simplified.

BRIEF DESCRIPTION OF THE DRAWINGS

FIG. 1 is a schematic illustration of one embodiment of a device of the invention.

DETAILED DESCRIPTION

The invention is explained in greater detail below as an example on the basis of exemplary embodiments illustrated in drawings. The single FIGURE shows a longitudinal section through a preferred delivery system with a stent in a schematic diagram.

To illustrate the invention, the FIGURE shows a longitudinal section through an exemplary preferred delivery system 10 for a medical device 44 according to the invention. The medical device 44 may be a stent, for example, in particular a self-expanding stent.

The delivery system 10 has a proximal end 12 and a distal end 14 with an inner shaft 30 extending between them. The inner shaft 30 encloses an inner lumen 32 in which a guide wire (not shown) is guided, facilitating the insertion of the medical device 44 designed as a stent. A handle piece 20 that serves as a holding handle for the delivery system is arranged on the proximal end 12.

An outer shaft 40 surrounds the inner shaft 30 in at least some areas. The outer shaft 40 surrounds an intermediate lumen 42 between the outside of the inner shaft 30 and the inside of the outer shaft 40. The outer shaft 40 extends only up to the holding handle 20 and is designed in several parts. The outer shaft 40 consists of the component parts 40a, 40b, 40c. The distal component part 40c surrounds the medical device 44 on insertion, the middle component part 40b surrounds a middle area of the inner shaft relatively tightly and the proximal component part 40a abuts against the handle piece 20. The intermediate lumen 42 has different radial dimensions along the inner shaft 30 according to the inside diameters of the component parts 40a, 40b, 40c of the outer shaft 40.

The medical device 44 designed as a stent is situated inside the third component part 40c of the outer shaft 40 and is supported in a compressed form in the intermediate lumen 42 at the distal end 14 with the usual retaining means and the like. Furthermore, a tip 50 is arranged on the distal end 14 with a guide wire (not shown) guided in the tip in a wire lumen 52 which extends continuously from the tip 50 to an access 28 on the proximal end 12. In the insertion process, the guide wire protrudes out of the free end of the coupling device 26.

With the help of the handle piece 20 on the proximal end 12 the outer shaft 40 can be retracted to release the medical device 44, which is embodied as a stent. A securing sleeve 22, which is removable for release, is arranged between the handle piece 20 and the proximal end 12 to secure the relative position of the inner shaft 30 to the outer shaft 40. A marking element 16 serves to indicate whether or not the medical device 44 has been released entirely when the medical device 44 is released.

The inner shaft 30 is formed by a metal shaft 30a, for example, on the proximal end 12 for better handling with the marking element 16 arranged on the metal shaft.

A coupling device 26 on the handle piece 20 is attached to the proximal end 12 and has an access 28 through which the inner lumen 32 and the intermediate lumen 42 can be rinsed with a fluid, e.g., a saline solution, and/or vented. The securing sleeve 22 is arranged between the handle piece 20 and the coupling device 26.

A seal (not shown) is provided on the proximal end of the holding handle 20, so that the fluid for rinsing cannot escape proximally but instead can escape only at the distal end 14.

The inner shaft 30 has at least one first opening 34 in the area of the first component piece 40a of the outer shaft 40 near to the proximal end 12 and has at least one second opening 36 on the distal end 14, so that a fluid connection is formed between the inner lumen 32 and the intermediate lumen 42. The fluid is supplied through the access 28 of the coupling device 26 into the inner lumen 32 of the inner shaft 30 and can escape through the openings 34 and 36 into the intermediate lumen 42. The fluid can escape out of the intermediate lumen 42 to the outside at the transition 46 between the third component piece 40c of the outer shaft 40 and the tip 50 at the distal end because the outer shaft 40 does not abut against the tip 50 with a seal.

The rinsing and/or venting of the inner lumen 32 and the intermediate lumen 42 may advantageously be performed in a single operation from the coupling piece 26.

What is claimed is:

1. A delivery system for a medical device, comprising:
   a stent having a proximal end and a distal end,
   an inner shaft which encloses an inner lumen having axial openings at proximal and distal ends of the inner shaft, and
   an outer shaft which surrounds the inner shaft in at least one area and encloses an intermediate lumen, the intermediate lumen being an area disposed between an inner surface of the outer shaft and an outer surface of the inner shaft,
   wherein a plurality of side openings are formed in the inner shaft, each of the plurality of side openings establishing a fluid connection between the inner lumen and the intermediate lumen, at least a first one of the plurality of side openings being disposed adjacent to the proximal end of the inner shaft, a second one of the plurality of side openings being disposed adjacent to a distal end of the inner shaft,
   and wherein the outer shaft comprises a plurality of separate component parts, at least one of the plurality of component parts having a different inner diameter than others of the plurality of component parts, a portion of the intermediate lumen defined between the outer surface of the inner shaft and an inner surface of each of the plurality of outer shaft sections,
   wherein a distal one of the plurality of component parts surrounds the stent and the second one of the plurality of openings and the stent surrounds the second one of the plurality of openings, wherein a proximal one of the plurality of component parts abuts a handle piece and surrounds the first one of the plurality of side openings, and one or more central ones of the plurality of component parts tightly surrounds a central portion of the inner shaft, and
   wherein the inner diameter of the proximal and distal component parts are approximately equal, and the inner diameter of the central component part is smaller than the inner diameters of the proximal and distal component parts.

2. The delivery system according to claim 1, characterized in that
   a coupling device is provided on the proximal end of the handle piece for at least one of rinsing and venting a fluid of the inner lumen and the intermediate lumen.

3. The delivery system according to claim 2, characterized in that
   the coupling device is arranged on the handle piece of the inner lumen.

4. The delivery system according to claim 1, wherein the intermediate lumen has different radial dimensions based on the different inner diameters of the separate component parts of the outer shaft.

5. The delivery system according to claim 1, further comprising a coupling device disposed at the proximal end of the system, the coupling device having an access port in direct communication with the inner lumen, and in communication with the intermediate lumen, the access port configured to allow fluid to flow from outside the system into the inner lumen.

6. The delivery system according to claim 5, wherein the coupling device is attached to the handle piece, and wherein a seal is formed at a joint of the coupling device and the handle piece to prevent fluids from escaping at the joint.

7. The delivery system according to claim 1, wherein an outside diameter of the central component part is approximately equal to inside diameters of the distal component part and the proximal component part, such that an outer surface of the central component part is engaged with respective inner surfaces of the distal component part and the proximal component part.

8. The delivery system according to claim 1, wherein the handle piece includes an annular shoulder on an inner wall configured to receive a proximal end of the proximal component part.

9. The delivery system according to claim 1, wherein the outer shaft at least partially defines a gap configured to allow passage of fluid from the intermediate lumen to outside of the delivery system.

10. The delivery system according to claim 1, further comprising a securing sleeve configured to secure a position of the inner shaft relative to the outer shaft.

11. The delivery system according to claim 10, wherein the securing sleeve is disposed at a proximal end of the delivery system and includes a marking element indicating whether the stent has been fully released.

12. A delivery device for delivering a medical device to a predetermined location, the delivery device comprising:
    a generally cylindrical inner shaft having proximal and distal ends and a sidewall extending therebetween, the inner shaft defining an inner lumen extending axially through the inner shaft, the inner lumen including axial openings at the proximal and distal ends of the inner shaft;
    an outer shaft having proximal and distal ends and surrounding at least a portion of the inner shaft, an intermediate lumen defined between the outer shaft and the inner shaft; and
    a coupling device disposed at the proximal end of the inner and outer shafts, the coupling device including an access port in fluid communication with the inner lumen;
    wherein the sidewall of the inner shaft defines a plurality of side openings, each of the side openings establishing fluid communication between the inner lumen and the intermediate lumen, at least one of the plurality of side openings being disposed adjacent to the proximal end of the inner shaft;
    wherein the outer shaft is divided axially into a proximal component part, a central component part, and a distal component part, each component part sized such that an outside diameter of the central component part is approximately equal to inside diameters of the distal component part and the proximal section, so that an outer surface of the central component part is engaged with respective inner surfaces of the distal component part and the proximal component part, portions of the intermediate lumen defined between each of the proximal, central, and distal outer shaft component parts and the inner shaft sidewall;

wherein the medical device is disposed in the intermediate lumen between the inner shaft and the distal component part of the outer shaft surrounding one of said side openings; and wherein the intermediate lumen has different radial dimensions based on the different inner diameters of the proximal, central, and distal component part of the outer shaft.

13. The delivery system according to claim 12, further comprising a securing sleeve disposed at a primal end of the delivery system and configured to secure a position of the inner shaft relative to the outer shaft, the inner shaft including a marking element indicating whether the medical device has been fully released.

14. A delivery system for a medical device, comprising:
a stent having a proximal end and a distal end;
a catheter having an inner shaft and an outer shaft;
a coupling device disposed at the proximal end of the inner and outer shafts;
a generally cylindrical handle piece disposed between the coupling device and the inner and outer shafts;
a securing sleeve disposed at a proximal end of the delivery system for securing relative positions of the inner shaft and outer shaft; and
a tapered tip disposed at a distal end of the system,
wherein the outer shaft is divided into a plurality of separate component parts, at least one of the sections having a different inner diameter than others of the plurality of component parts, an intermediate lumen defined between an outer surface of the inner shaft and inner surfaces of the plurality of component parts of the outer shaft, and wherein the inner diameter of proximal and distal ones of the plurality of component parts are approximately equal, and the inner diameter of a central one of the plurality of component parts is smaller than the inner diameters of the proximal and distal ones of the plurality of component parts,
wherein the inner shaft encloses an inner lumen having axial openings at proximal and distal ends of the shaft, the inner shaft further including a plurality of side openings formed in the inner shaft and establishing fluid communication between the inner lumen and the intermediate lumen, at least a first one of the side openings being disposed adjacent to the proximal end of the inner shaft and a second one of the side openings being disposed adjacent the distal end of the inner shaft,
wherein the stent is disposed in the intermediate lumen surrounding the second one of the side openings,
wherein the coupling device includes an access port in fluid communication with the inner lumen,
and wherein the inner shaft includes a marking element indicating whether the stent has been fully released.

* * * * *